US012290395B2

(12) United States Patent
Eguchi (10) Patent No.: US 12,290,395 B2
(45) Date of Patent: May 6, 2025

(54) RADIOGRAPHY DEVICE, RADIATION DEVICE, RADIOGRAPHY SYSTEM, AND MOBILE RADIOGRAPHY SYSTEM

(71) Applicant: Konica Minolta, Inc., Tokyo (JP)

(72) Inventor: Mao Eguchi, Kokubunji (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 18/601,160

(22) Filed: Mar. 11, 2024

(65) Prior Publication Data

US 2024/0255905 A1    Aug. 1, 2024

Related U.S. Application Data

(63) Continuation of application No. 17/546,544, filed on Dec. 9, 2021, now Pat. No. 11,957,500.

(30) Foreign Application Priority Data

Dec. 24, 2020    (JP) .................. 2020-214570

(51) Int. Cl.
*A61B 6/00*    (2024.01)
*A61M 5/00*    (2006.01)
(Continued)

(52) U.S. Cl.
CPC ............... *A61B 6/542* (2013.01); *A61M 5/00* (2013.01); *A61M 5/1723* (2013.01);
(Continued)

(58) Field of Classification Search
CPC ......... A61B 6/542; A61B 6/56; A61B 6/4283; A61B 6/54; A61B 6/44; A61M 5/00; A61M 5/1723; G05B 15/02; G16H 20/10
See application file for complete search history.

(56) References Cited

U.S. PATENT DOCUMENTS

2016/0174350 A1    6/2016  Tamura et al.
2017/0156687 A1    6/2017  Hosoki et al.
(Continued)

FOREIGN PATENT DOCUMENTS

JP    2006-305106 A    11/2006
JP    2017-099784 A    6/2017
(Continued)

OTHER PUBLICATIONS

Office Action dated Aug. 30, 2022 for the related Japanese Patent Application No. 2020-214570, with English translation.
(Continued)

*Primary Examiner* — Courtney D Thomas
(74) *Attorney, Agent, or Firm* — LUCAS & MERCANTI, LLP (57) ABSTRACT

A radiography device includes an interface unit and a controller. The interface unit connects to an external interface. The controller operates according to timing signals from the external interface connected to the interface unit so as to synchronize with timing of repetition of generation of radiation by a radiation device that generates radiation in serial radiography in which frame images are generated. Even after connection between the interface unit and the external interface is cut off, the controller repeats operation for generating a frame image while synchronizing with the radiation device without communicating with an outside.

8 Claims, 3 Drawing Sheets

(51) Int. Cl.
*A61M 5/172* (2006.01)
*G05B 15/02* (2006.01)
*G16H 20/10* (2018.01)

(52) U.S. Cl.
CPC ............. *G05B 15/02* (2013.01); *G16H 20/10* (2018.01); *A61B 6/56* (2013.01)

(56) References Cited

U.S. PATENT DOCUMENTS

2020/0008771 A1   1/2020  Isogai et al.
2022/0000440 A1*  1/2022  Eguchi .................. A61B 6/464

FOREIGN PATENT DOCUMENTS

| JP | 2017-136187 A | 8/2017 |
| JP | 2019-166107 A | 10/2019 |
| JP | 2020-005881 A | 1/2020 |

OTHER PUBLICATIONS

JPO, Office Action for the related Japanese Patent Application No. 2020-214570, dated Apr. 26, 2022, with English translation.
Office Action, dated Mar. 14, 2025, issued for the corresponding Chinese Patent Application No. 202111567845.5, 20 pages, with English translation.

\* cited by examiner

RADIOGRAPHY DEVICE, RADIATION DEVICE, RADIOGRAPHY SYSTEM, AND MOBILE RADIOGRAPHY SYSTEM

CROSS-REFERENCE TO RELATED APPLICATIONS

This application is a continuation of U.S. patent application Ser. No. 17/546,544 filed Dec. 9, 2021, which claimed the priority of Japanese Patent Application No. 2020-214570 filed on Dec. 24, 2020, which is incorporated herein by reference in its entirety.

BACKGROUND

1. Technological Field

The present invention relates to a radiography device, a radiation device, a radiography system, and a mobile radiography system.

2. Description of the Related Art

In a conventional proposed radiography system, a radiation device that generates radiation and a radiography device that generates radiation images operate in synchronization with each other even when they are not connected by a cable.

For example, an X-ray imaging device described in JP 2006-305106A includes:
 a cable-less radiography section equipped with two-dimensional X-ray detection means for receiving X-rays transmitted through a subject; and
 a control device that controls imaging of a generator.

The X-ray imaging device is synchronized with the radiography control device or the generator for information on an available period of the radiography section. Then, each of them has the information on the available period of the radiography section in a built-in timer.

A control system described in JP 2020-005881A includes:
 a first timekeeper that periodically generates first timekeeping information in conjunction with one of a radiation device and a radiography device;
 a second timekeeper that periodically generates second timekeeping information in conjunction with the other device;
 a transmitter that transmits the first timekeeping information to the second timekeeper; and
 an adjuster that adjusts operation of at least one of the timekeepers in accordance with adjustment conditions while the second timekeeper does not acquire the first timekeeping information.

However, the X-ray imaging device described in JP 2006-305106A is for still radiography. The X-ray imaging device applies radiation once in response to one operation of a switch by a user. Therefore, a user has to operate or control the switch many times to apply radiation repeatedly.

Furthermore, the switch is usually operated in two steps. When the second step is performed, radiation begins to be applied. Therefore, when radiation is repeatedly applied, time intervals of radiation are sometimes too long. Thus, the technology described in JP 2006-305106A is not suitable for capturing a movie consisting of multiple frame images (hereinafter referred to as "serial radiography").

The control system described in JP 2020-005881A is different from the technology described in JP 2006-305106A in that it supports serial radiography.

However, in the control system described in JP 2020-005881A, each device generates its own clock. The timekeeping information must be adjusted in the absence of a reference. However, a specific means of performing the adjustment is unlikely to be derived from the content of JP 2020-005881A. Thus, the method of correcting clock deviation described in JP 2020-005881A is not feasible. The timekeeping information may not be sufficiently adjusted.

SUMMARY

The present invention was made in view of the above problems. An object of the present invention is to stably perform serial radiography that generates frame images even when a radiation device that generates radiation and a radiography device that generates radiation images are not connected by an interface such as a cable.

To achieve the above object, according to an aspect of the present invention, a radiography device includes:
 an interface unit that connects to an external interface; and
 a controller that operates according to timing signals from the external interface connected to the interface unit so as to synchronize with timing of repetition of generation of radiation by a radiation device that generates radiation in serial radiography in which frame images are generated,
 wherein, even after connection between the interface unit and the external interface is cut off, the controller repeats operation for generating a frame image while synchronizing with the radiation device without communicating with an outside.

BRIEF DESCRIPTION OF DRAWINGS

The advantages and features provided by one or more embodiments of the invention will become more fully understood from the detailed description given hereinbelow and the appended drawings which are given by way of illustration only, and thus are not intended as a definition of the limits of the present invention.

DETAILED DESCRIPTION OF EMBODIMENTS

Hereinafter, embodiments of the present invention will be described with reference to the drawings. The scope of the claims of the invention is not limited to examples shown in the drawings.

1. Radiography System

Figure 1:
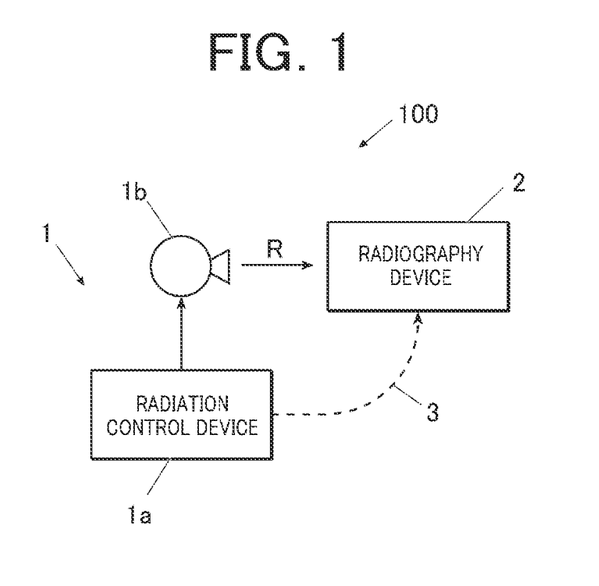
FIG. 1 is a block diagram showing a radiography system according to an embodiment of the present invention.

First, a schematic configuration of a radiography system (hereinafter referred to as radiography system 100) according to the embodiment will be described. FIG. 1 is a block diagram representing a schematic configuration of the radiography system 100.

1-1. Schematic Configuration of Radiography System

As shown in FIG. 1, the radiography system 100 of the present embodiment includes:
 a radiation device (hereinafter referred to as radiation device 1);
 one or more radiography devices (hereinafter referred to as radiography devices 2); and
 an external interface (hereinafter referred to as external IF).

Radiation Device

The radiation device 1 generates radiation R (e.g., X-ray) to irradiate a subject and the radiography device 2 behind the subject with the radiation R. The radiation device 1 includes a radiation control device (hereinafter referred to as control device 1a) and a tube 1b.

A specific configuration of the control device 1a will be described later.

Radiography Device

The radiography device 2 generates image data by receiving radiation R from the radiation device 1. The radiography device 2 communicates with the radiation device 1.

A specific configuration of the radiography device 2 will be described later.

External Interface

The external IF communicatively connects, for example, the radiation device 1 or a control device (not shown) and the radiography device 2.

For example, the external IF includes:
 a communication cable 3;
 a cradle into which the radiography device 2 is inserted; and
 a housing 6 in a medical vehicle which houses the radiography device 2.

The external IF can be disconnected (e.g., unplugged) from at least one of the radiation device 1 and the radiography device 2, if necessary.

1-2. Schematic Operation of Radiography System

In the radiography system 100 of the embodiment having the above configuration, the radiation device 1 irradiates, with radiation R, a subject disposed between the radiation device 1 and the radiography device 2. Thereby, the radiography system 100 radiographs the subject.

The radiography system 100 of the present embodiment can shoot video (hereinafter referred to as serial radiography). Based on a single radiography operation (pressing of a radiation command switch not shown), the radiation device 1 generates pulsed radiation R of a preset time width a plurality of times in succession at regular intervals. The radiography device 2 generates frame images that constitute a video.

The radiography system 100 may communicate with an analysis device or other systems, such as a radiology information system (RIS) or a picture archiving and communication system (PACS).

2. Radiation Device

Figure 2:
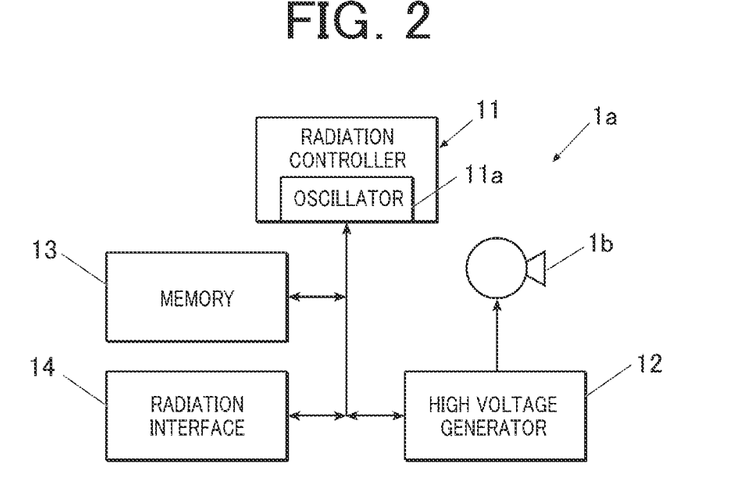
FIG. 2 is a block diagram showing a specific configuration of a radiation device provided in the radiography system of FIG. 1.

Next, details of the control device 1a provided in the radiation device 1 will be described. FIG. 2 is a block diagram showing a specific configuration of the control device 1a.

2-1. Specific Configuration of Radiation Device

As shown in FIG. 2, the control device 1a is constituted by a radiation controller 11, a high voltage generator 12, memory 13, a radiation interface (hereinafter referred to as radiation IF 14), and the like.

These components 11-14 of the control device 1a are powered by a power cable or a built-in power supply (not shown).

The radiation controller 11 includes a CPU and RAM. The radiation controller 11 comprehensively controls operation of the components 12-14 of the radiation device 1.

The radiation controller 11 includes an oscillator (hereinafter referred to as radiation oscillator 11a). The radiation oscillator 11a may be constituted by a crystal oscillator, a ceramic oscillator, or the like that generates a clock of a predetermined period when the device is turned on.

The radiation oscillator 11a of the embodiment generates a clock with accuracy higher than 100 ppm (e.g., 10 ppm).

Time may be kept by a timekeeper separate from the radiation oscillator 11a.

The high voltage generator 12 applies a voltage to the tube 1b in accordance with preset radiography conditions in response to receipt of a timing signal from the radiation controller 11.

For example, the radiography conditions include:
 a radiography mode (still radiography or serial radiography);
 conditions related to a subject, such as a part to be radiographed and build; and
 conditions related to radiation of radiation R, such as a tube voltage, a tube current, a radiation time, and a current-time product.

The radiography mode included in the radiography conditions is information about a radiography method, such as still radiography or serial radiography. The system 100 can set the radiography mode in advance. The high voltage generator 12 operates in accordance with a setting of the radiography mode.

In a case where serial radiography is included in the radiography conditions, pulsed voltage is repeatedly applied at predetermined intervals each time a timing signal is received.

When a voltage is applied from the high voltage generator 12, the tube 1b generates radiation R with a dose corresponding to the applied voltage. Specifically, the tube 1b radiates pulsed radiation R in response to pulsed voltage applied by the high voltage generator 12.

The memory 13 is constituted by a HDD (hard disk drive), semiconductor memory, or the like. The memory 13 stores various processing programs as well as parameters and files necessary for executing the programs.

The memory 13 stores various data generated in processing by the radiation controller 11 such as timekeeping information, which will be described later.

The radiation IF 14 can be connected to the external IF. The radiation IF 14 performs at least one of transmission and reception of various information (signals and data).

Specifically, the radiation IF 14 includes:
 a connector into which the communication cable 3 is plugged;
 an antenna that transmits and receives radio waves;
 a lamp that emits light (including infrared light) or an optical sensor that detects light;
 a speaker that emits sound (including ultrasound) or a microphone that detects sound;
 a transducer that transmits vibration to a device (such as the radiography device 2) that comes into contact with it, or a vibration sensor that detects vibration; and
 a coil that generates a magnetic field.

A configuration of the radiation IF 14 is determined according to transmission format for information.

2-2. Specific Operation of Radiation Device

The radiation controller 11 of the radiation device 1 thus configured operates as follows according to programs stored in the memory 13.

For example, the radiation controller 11 sets various radiography conditions.

The radiography conditions include:
- a radiography mode (still radiography or serial radiography);
- conditions related to a subject, such as a part to be radiographed and build; and
- conditions related to radiation of radiation R, such as a tube voltage, a tube current, a radiation time, a current-time product, and a frame rate.

The radiation controller 11 generates, for the high voltage generator 12, a timing signal that triggers application of voltage (radiation of radiation R) in response to reception of a signal that notifies pressing of a radiation command switch (not shown).

In a case where serial radiography is included in the radiography conditions, the timing signal is generated repeatedly at a cycle corresponding to a frame rate.

3. Configuration of Radiography Device

Figure 3:
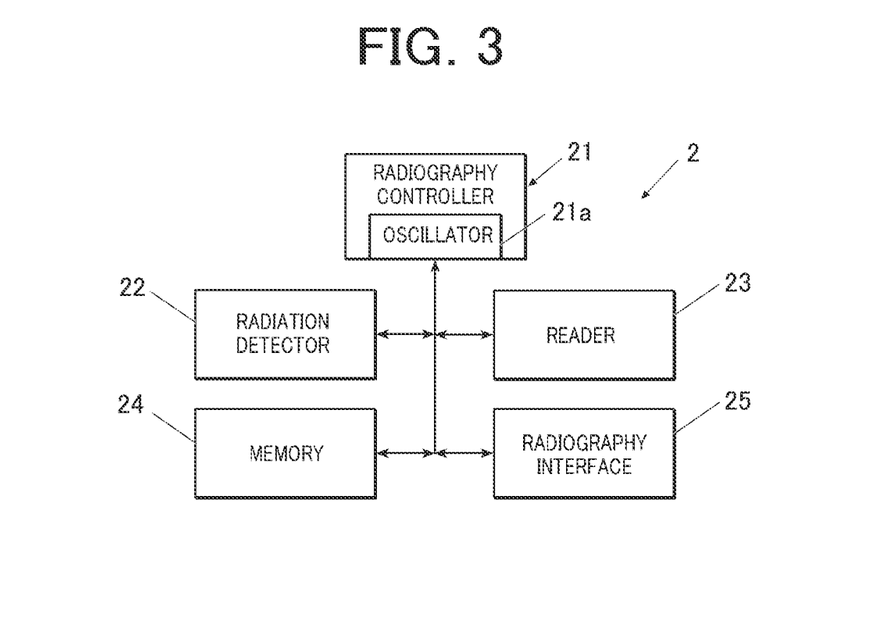
FIG. 3 is a block diagram showing a specific configuration of a radiography device provided in the radiography system of FIG. 1.

Next, a specific configuration of the radiography device 2 provided in the radiography system 100 will be described. FIG. 3 is a block diagram showing a specific configuration of the radiography device 2.

3-1. Specific Configuration of Radiography System

As shown in FIG. 3, the radiography device 2 of the embodiment includes a radiography controller 21, a radiation detector 22, a reader 23, memory 24, a radiography interface (hereinafter referred to as radiography IF 25) in addition to a case (not shown).

These components 21-25 of the radiography device 2 are powered by a power cable or a built-in power supply (not shown).

The radiography controller 21 comprehensively controls operation of the components 22-25 of the radiography device 2 with a CPU, RAM, etc.

The radiography controller 21 includes an oscillator (hereinafter referred to as radiography oscillator 21a). The radiation oscillator 21a may be constituted by a crystal oscillator, a ceramic oscillator, or the like that generates a clock of a predetermined period when the device is turned on.

The radiography oscillator 21a of the embodiment generates a clock with accuracy higher than 100 ppm (e.g., 10 ppm) like the radiation oscillator 11a.

Time may be kept by a timekeeper separate from the radiography oscillator 21a.

The radiation detector 22 includes:
- radiation detector elements that each generate, directly or indirectly, an electric charge corresponding to a dose of radiation R received from an external source;
- a switch element provided between each radiation detector element and wiring to switch between:
  - an ON state in which a current can be passed between the radiation detector and the wiring; and
  - an OFF state in which a current cannot be passed; and
- a substrate on which pixels are arranged in a two-dimensional pattern.

Known radiation detectors can be used.

The radiography device 2 may be of a so-called indirect type. An indirect radiography device includes a scintillator. The scintillator emits light when it receives radiation R. The radiography device detects the light. Alternatively, the radiography device 2 may be of a so-called direct type. A direct type radiography system detects radiation R directly without a scintillator, etc.

The reader 23 reads a signal value corresponding to an amount of charge accumulated in each of the radiation detector elements (generated by the radiation detector elements). The reader 23 generates image data of a radiation image based on each signal value. Known readers can be used.

The memory 24 is constituted by a HDD (hard disk drive), semiconductor memory, or the like.

The memory 24 stores:
- various processing programs including various image processing programs; and
- parameters and files required to run the program.

The memory section 24 stores various data generated in processing by the radiography controller 21 such as timekeeping information, which will be described later.

The radiography IF 25 can be connected to the external IF. The radiography IF 25 performs at least one of transmission and reception of various information (signals and data). In a case where the radiation IF 14 performs only one of transmission and reception, the radiography IF 25 can perform at least the other.

Specifically, the radiography IF 25 includes:
- a connector into which the communication cable 3 is plugged;
- an antenna that transmits and receives radio waves;
- a lamp that emits light (including infrared light) or an optical sensor that detects light;
- a speaker that emits sound (including ultrasound) or a microphone that detects sound;
- a transducer that transmits vibration to a device (such as the radiation device 1) that comes into contact with it, or a vibration sensor that detects vibration; and
- a coil that generates a magnetic field.

A configuration of the radiography IF 25 is determined according to a configuration of the radiation IF 14.

In a case where the radiography device 2 is powered by a built-in power supply, the built-in power supply can be a lithium ion capacitor (LiC), a lithium ion battery (LiB), or another power supply.

Lithium ion capacitors can be charged quickly and do not ignite. Therefore, after radiography (e.g., mobile radiography), the next radiography can be performed immediately.

On the other hand, lithium-ion batteries are inexpensive and have a large capacity. It reduces a manufacturing cost for the radiography device 2 and also reduces the number of times a battery needs to be recharged. Both configurations are desirable for taking multiple radiographs.

3-2. Specific Operation of Radiography System

The radiography controller 21 of the radiography device 2 thus configured operates as follows according to programs stored in the memory 24.

For example, the radiography controller 21 has a function of switching a state of the radiography device 2 to one of an "initialization state", an "accumulation state", and a "read/transfer state".

Timing for switching the states will be described later.

The "initialization state" is a state where:
- an ON voltage is applied to each switch element; and
- a charge generated by the radiation detector elements is not stored in each pixel, i.e., the charge is released to a signal line.

The "accumulation state" is a state where:
an OFF voltage is applied to each switch element; and
a charge generated by the radiation detector element can be stored in a pixel, i.e., no charge is released to a signal line.

The "read/transfer state" is a state where:
an ON voltage is applied to each switch element; and
the reader 23 is driven to read a signal value based on a flowed-in charge.

The radiography controller 21 makes a period of the accumulation state (period to accumulate an electric charge generated by the radiation detector element) longer than before. Alternatively, the radiography controller 21 shortens a period of the read/transfer state (time required for reading of a signal value by the reader 23).

Repetition of operation of returning to the initialization state before performing serial radiography consumes a lot of power.

Therefore, the radiography device 2 may start repeating the operation of returning to the initialization state before serial radiography in response to predetermined operation by a user. Alternatively, the radiography device 2 may set a period corresponding to a workflow as a "wait" period. The radiography device 2 starts to operate automatically after the "wait" period.

It reduces consumption of power in a whole workflow.

4. Synchronization of Signals

Next, synchronization of timing signals in the above-described radiography system 100 will be described.

4-1. Operation Common to Parent Device and Child Device

First, the radiation controller 11 of the radiation device 1 has a function of periodically generating timekeeping information using a clock generated by the radiation oscillator 11a.

The generated timekeeping information includes timing signals and time information.

The timing signals are pulse signals, etc. which are output when one or more clocks are generated.

The time information is, for example, a count value of a timer that counts up according to a clock.

The components 11-14 of the radiation device 1 operate based on a clock generated by the radiation oscillator 11a.

The radiography controller 21 of the radiography device 2 also has a function of periodically generating timekeeping information using a clock generated by the radiography oscillator 21a.

A format of the generated timekeeping information should preferably be adapted to timekeeping information generated by the radiation device 1.

The components 21-25 of the radiography device 2 operate based on the clock generated by the radiography oscillator 21a.

4-2. Operation of Parent Device

Of the radiation controller 11 and the radiography controller 21, a controller of a parent device transmits generated timekeeping information to a child device.

This function of transmitting timekeeping information is effective when the radiation IF 14 of the radiation device 1 and the radiography IF 25 of the radiography device 2 are connected.

For example, a connection state is:
a state where a connector at one end of the communication cable 3 is plugged into a connector of the radiation IF and where a connector at the other end of the communication cable 3 is plugged into a connector of the radiography IF (wired connection);
a state where an antenna provided in one IF is close to an antenna in the other IF;
a state where a lamp provided in one IF is close to a light sensor in the other IF (including a state where they are connected with an optical cable);
a state where a speaker of one IF is close to a microphone of the other IF;
a state where a coil of one IF is close to a coil of the other IF; or
a state where a transducer of one IF is in contact with a sensor of the other IF.

In a case where timekeeping information is transmitted through wired communication through a communication cable 3 connecting the radiation device 1 and the radiography device 2, for example, a protocol such as NTP (network time protocol) or a method specified in the international standard IEEE Std. 1588-2008 (hereinafter referred to as IEEE 1588) may be used.

A configuration for transmitting the timekeeping information to the child device includes both of:
a configuration in which the radiation device 1 which is the parent device and the radiography device 2 which is the child device are connected by the communication cable 3, and in which current information (timing signals, etc.) of the radiation device 1 is transmitted to the radiography device 2 via the communication cable; and
a configuration in which the radiography device 2 and the radiation device 1 are the parent device and the child device, respectively, and in which current information of the radiography device 2 is transmitted to the radiation device 1 via the communication cable.

Of these configurations, according to the configuration in which the radiation device 1 is the parent device (and the radiography device 2 is the child device), the radiation device 1 usually has a function of transmitting timekeeping information to the child device. Alternatively, the function is achieved only by changing software.

On the other hand, according to the configuration in which the radiography device 2 is the parent device (and the radiation device 1 is the child device), to achieve a function of transmitting timekeeping information to the child device, sometimes hardware must be changed. For example, the radiography IF 25 is modified or replaced so that it can output current information.

4-3. Configuration of Child Device

A synchronization period is set for the child device. The synchronization period is a period during which the IF keeps synchronizing with the parent device while connection between the IF and the external IF is released.

4-4. Operation of Connected Child Device

When the controller of the child device which is one of the radiation controller 11 and the radiography controller 21 receives timekeeping information from the parent device, the controller of the child device corrects its own timekeeping information at the time of receiving the timekeeping information based on the received timekeeping information.

Specifically, the controller of the child device generates a copy signal based on a timing signal transmitted from the parent device. Timing of rise of the copy signal is the same as that of the timing signal.

Accuracy of synchronization between timing signals of the radiation device 1 and the radiography device 2 decreases with the passage of time if no measure is taken. This is due to individual difference between the oscillators 11a, 21a and to difference between their temperature characteristics. However, the above operation reduces degradation of accuracy of synchronization.

The controller of the child device may repeatedly generate a copy signal based on a timing signal repeatedly transmitted from the parent device while the external IF is connected to the IF.

More specifically, the controller of the child device starts generating a copy signal immediately after determining that the external IF is connected. Immediately after the controller determines that connection with the external IF has been cut off, it terminates generation of the copy signal.

If the copy signal is generated only once, accuracy of synchronization between the copy signal and the timing signal will be reduced. Repetition of generating a new copy signal prevents degradation of accuracy of synchronization while the external IF is connected to the IF.

Accordingly, while the external IF is connected to the IF, the controller of the child device operates based on the timing signal (timekeeping information) from the external IF connected to the IF, while synchronizing with timing of repetition of operation by the parent device.

4-5. Operation of Child Device after Disconnection

After connection between the IF and the external IF is cut off, the controller of the child device operates to generate a frame image based on a copy signal generated by itself.

Accordingly, even after connection between the IF and the external IF is cut off, the controller of the child device repeats operation for generating a frame image or operation of generating radiation R while synchronizing with the parent device without communicating with the external (parent device or other control device).

After connection between the IF and the external IF is cut off, accuracy of synchronization between a timing signal generated by the parent device and a copy signal generated by the child device decreases with the passage of time.

However, as described above, both the radiation oscillator 11a and the radiography oscillator 21a of the embodiment generate clocks with accuracy higher than 100 ppm. Therefore, even a relatively long time (e.g., about 30 minutes) after connection between the IF and the external IF is cut off, the child device keeps synchronizing with the parent device (a state where difference between a timing signal and a copy signal is within a range that does not affect image quality).

As described above, the radiography controller 21 makes a period for accumulating a charge generated by the radiation detector element (accumulation state) longer than before. Alternatively, the radiography controller 21 shortens a time required for reading of signal values by the reader 23. Thus, the radiography controller 21 widens an allowable range of difference between signals.

The child device can keep synchronizing with the parent device also by this.

In a case where the external IF is the communication cable 3, chattering or the like occurs when the cable is inserted into or removed from a connector of the child device. It may reduce accuracy of synchronization between timing signals of the radiation device 1 and the radiography device 2.

Therefore, the child device may include an anti-chattering circuit.

It prevents decrease in accuracy of synchronization between timing signals when the cable is inserted or removed.

4-6. Synchronization of Signals, Etc.

The system 100, which is devised to lengthen the synchronization period as described above, may have the following configuration.

For example, the controller of at least one of the parent device and the child device may regulate radiography (no radiography is allowed) when the synchronization period passes after connection between the IF and the external IF is cut off.

Radiography is performed only within the synchronization period in which images are not affected. It prevents deterioration of quality of radiographic images.

The controller of at least one of the parent device and the child device may notify a user via a notification unit 4 that radiography is not allowed or that the user is urged to connect the external IF to the IF when the synchronization period passes after connection between the IF and the external IF is cut off.

The notification unit 4 is a display, a speaker, a vibrator, or the like.

Figure 4:
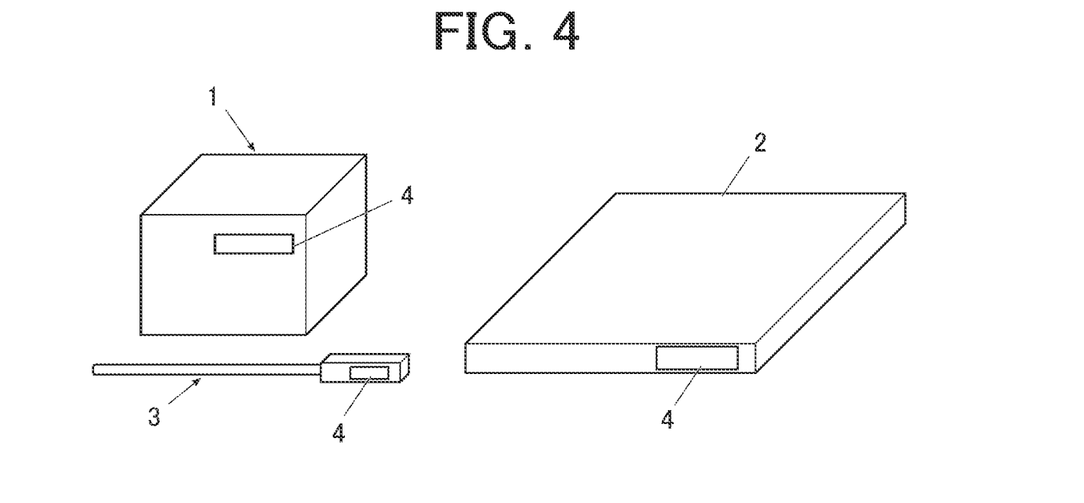
FIG. 4 is a diagram showing modification of the radiography system of FIG. 1.

As shown in FIG. 4, for example, a position where the notification unit 4 is provided can be any place in the system 100, such as the radiation device 1, the radiography device 2, and the communication cable 3, as long as it is visible to the user.

In a case where notification is performed after the synchronization period passes, the controller of at least one of the parent device and the child device may estimate whether it will be necessary to interrupt radiography in the future based on sequence of radiography orders and a remaining time (difference between the synchronization period and a time elapsed so far). The controller notifies a user of the estimation result in advance via the notification unit 4.

For example, it prevents repositioning while connecting the radiography device 2 to the external IF for synchronization after still radiography in order to perform serial radiography following still radiography.

Serial radiography could be performed without re-synchronization.

5. Mobile Radiography System

Figure 5:
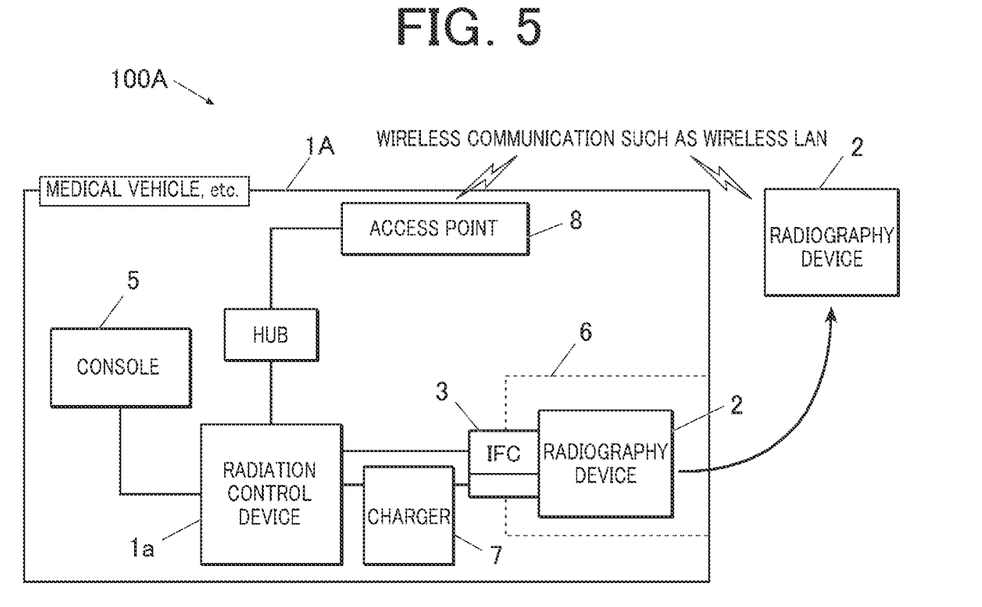
FIG. 5 is a block diagram showing an example of a mobile radiography system configured with the radiography system of FIG. 1.

Next, details of a mobile radiography system 100A in which the radiography system 100 is used will be described. FIG. 5 is a block diagram showing an example of the mobile radiography system 100A.

5-1. Background

To perform radiography using a radiography table installed in a radiography room of a hospital, communication cables and power cables are connected to the radiography device 2 installed on the table.

For example, it allows:

transmission and reception of information between the radiography device 2 and the radiation device 1; and supply of electric power to the radiography device 2.

For example, in a case where a communication cable is used for connection to the radiography device 2, pulse signals and timing signals are included in control signals of the communication cable. It makes it possible to synchronize timing of the radiation device 1 and the radiography device 2 in radiography.

However, for example in a radiography room, sometimes radiography has to be performed while a patient is on a wheelchair or a bed.

In such a case, radiography with the communication cable still connected to the radiography device 2 causes, for example:

a problem that the communication cable gets in the way;

a problem that there is a risk that the communication cable will come loose and communication will be lost; and a problem that the communication cable touches a subject to cause unsanitary environment.

Therefore, it was desired to perform radiography without a communication cable.

On the other hand, in a case where radiography is performed while moving with the mobile radiography system 100A, radiography is performed in a ward where a subject stays. In that case, radiography is performed in a bed where the subject is lying. The radiography device 2 is taken out of the housing 6. The radiography device 2 is placed between the subject and the bed, and radiography is performed.

Compared to the case where radiography takes place in a radiography room, this case is more likely to cause:
 a problem that the communication cable gets in the way;
 a problem that there is a risk that the communication cable will come loose and communication will be lost; and
 a problem that the communication cable touches a subject to cause unsanitary environment.

Therefore, it was desired to perform radiography without a communication cable.

Especially in radiography using computed radiography (CR), no communication cable is required during radiography. It was also desired to perform radiography using the radiography device 2 without a communication cable in order to obtain the same ease of operation as in CR.

Therefore, the radiography system 100 of the present embodiment which has the above-described configuration can also be used as the mobile radiography system 100A.

Of course, it is also possible to install and use the radiography system 100 in a radiography room of a hospital, etc.

5-2. Specific Configuration of Mobile Radiography System

As shown in FIG. 5, the mobile radiography system 100A includes a medical vehicle 1A and the radiography device 2. The tube 1b is not shown in FIG. 5.

The mobile radiography system 100A of the embodiment includes a plurality of radiography devices 2.

As described above, the synchronization period is set for the radiography devices 2. Accordingly, the synchronization period is also set for each of the radiography devices 2 included in the mobile radiography system 100A.

At least one (but not all) of the radiography devices 2 may be not the radiography device described above but an existing radiography device, which can hardly keep synchronization as soon as connection to the external IF is cut off.

The medical vehicle 1A includes a console 5, the housing 6, and wheels (not shown) in addition to the control device 1a. The medical vehicle 1A can move.

The medical vehicle 1A of the embodiment further includes a charger 7 and an access point 8.

The console 5 can set radiography conditions for at least one of the control device 1a and the radiography device 2 based on:
 radiography orders obtained from other systems (HIS, RIS, etc.); and
 operation made by a user (e.g. radiographer) on an operation interface (not shown).

The radiography conditions include a radiography mode (still radiography or serial radiography), a tube voltage, a product of a tube current and a radiation time or a current time (mAs value), a portion to be radiographed, and a radiography direction.

The console 5 acquires image data of the radiographic image generated by the radiography device 2. The console 5 stores it in itself or transmits it to other devices, such as a PACS and a dynamic analysis device.

The housing 6 stores the radiography device 2.

The housing 6 in the embodiment stores a plurality of radiography devices 2.

The housing 6 has the external IF that is connected to the radiography IF 25 when the radiography device 2 is stored. Specifically, a tip of the communication cable 3 is attached to a point which is inside the housing 6 and which is opposite the radiography IF 25.

The housing 6 may have a plurality of external IFs so that it can be connected to a radiography IF 25 of each of the stored radiography devices 2. It allows the medical vehicle 1A to synchronize with the radiography devices 2 simultaneously.

Which connections are to the external IFs that can be synchronized may be changed according to configuration of the medical vehicle 1A.

For example, it may be only the storage 6, or only the communication cable 3, or all connections.

It increases choice of the external IFs to be synchronized and improves usability.

The housing 6 may be capable of storing the radiography device 2 to which a shield member is attached. For example, the shield member is a cap-type grid. It has a large number and grid irregularity appears in high frequency.

It may be possible to charge the built-in power supply, synchronize timing signals, etc. simultaneously.

In that case, the radiography device 2 can be stored in the housing 6 without removing the shield member. It reduces stress of a user.

In the case where the shield member is the cap-type grid, noise (electromagnetic noise and scattered radiation) is prevented from flowing into the radiography device 2. For example, shifting of an angle of the shield member (grid) with respect to the radiography device 2 is prevented when radiography is performed while the radiography device 2 is inserted into a back of a patient or when the radiography device 2 is stored. As a result, processing of calculating an angle of the grid based on a radiographic image can be omitted from image processing of removing the grid from the radiographic image.

The charger 7 charges the built-in power supply of the radiography device 2.

The charger 7 may charge the built-in power supply by being supplied with power from an external power source (e.g., an outlet in a hospital). Alternatively, the charger 7 may charge the built-in power supply by being supplied with power from a power source provided in the medical vehicle 1A. The charger 7 may charge the built-in power supply using its own power source.

A required amount of power is set for the medical vehicle 1A.

The required amount of power is an amount of power required for the radiography device 2 to perform predetermined radiography, which is an amount of power supplied from the built-in power supply when the radiography device 2 performs predetermined radiography.

A plurality of required amounts of power is set for the medical vehicle 1A according to the embodiment.

The required amount of power depends on at least one of:
 a type of predetermined radiography;
 a radiography time in a case where a type of predetermined radiography is serial radiography; and
 an IF in a case where a type of predetermined radiography is serial radiography.

5-3. Operation of Mobile Radiography System

In the mobile radiography system 100A of the embodiment having the above-described configuration, the radiation controller 11 of the medical vehicle 1A operates as follows, for example.

For example, the radiation controller 11 selects the radiography device 2 to be used from the plurality of radiography devices 2 in response to operation to, for example, the console 5 by a user.

The radiation controller 11 manages an elapsed time after connection between the external IF and the IFs of the radiography devices 2 is cut off.

Then, the radiation controller 11 permits radiography in a case where a radiography device for which the synchronization period has not passed after connection between the IF and the external IF is cut off is selected from the plurality of radiography devices 2.

While the external IF is connected to the radiography IF 25 of the radiography device 2, the radiation controller 11 makes the charger 7 charge the built-in power supply of the radiography device 2.

In a case where a remaining power of the built-in power supply before predetermined radiography is less than a required amount of power, the radiation controller 11 may regulate the radiography.

In the case where a remaining power of the built-in power supply before predetermined radiography is less than a required amount of power, the radiation controller 11 may notify a user via the notification unit 4 that radiography is not allowed or that connection of the external IF to the IF is urged.

The radiation controller 11 may notify an estimated charging time via the notification unit 4.

It reduces risk of unnecessarily exposing a subject to radiation in re-radiography because a desired radiographic image cannot be obtained due to the built-in power supply running out in the middle of radiography.

In the case where notification is performed when a remaining power of the built-in power supply is less than a required amount of power, the controller of at least one of the parent device and the child device may estimate whether it will be necessary to interrupt radiography based on:

sequence of radiography orders acquired by the console 5; and a remaining power of the built-in power supply.

The controller notifies a user in advance of result of estimation via the notification unit 4.

For example, it prevents repositioning while connecting the radiography device 2 to the external IF for charging after still radiography in order to perform serial radiography following still radiography.

Serial radiography could be performed without charging.

The controller of one of the mobile vehicle 1A and the radiography device 2 may notify a user via the notification unit 4 to urge the user to store the radiography device 2 in the housing 6 of the medical vehicle 1A (to be connected to the external IF) upon completion of radiography, completion of examination, or the like.

Thus, even in a case where multiple radiography sessions are performed, a timing signal of the medical vehicle 1A is synchronized with a copy signal of the radiography device 2 in intervals between radiography sessions. The built-in power supply is charged.

It prevents subsequent radiography from becoming impossible.

Such an incident happens when:

the synchronization period passes in the middle of radiography; or a remaining power of the built-in power supply becomes less than a required amount of power.

Even in a case of still radiography, once connection to the external IF is cut off, the radiography device 2 continues to synchronize until it is connected to the external IF again.

Therefore, after connection between the IF and the external IF is cut off, it is desirable to set an operation mode of the radiography controller 21 to an operation mode with relatively low power consumption. It keeps synchronization longer. For example, the operation mode with low power consumption is a mode in which only operation of synchronizing timing signals is performed in the radiography controller 21 without operating the reader 23.

It prevents decrease in a remaining power of the built-in power supply. It prevents a situation in which radiography cannot take place due to insufficient remaining power of the built-in power supply even though it is within the synchronization period.

Once the radiography device 2 is connected to the external IF, it repeats generation of a copy signal until connection to the external IF is cut off again.

Therefore, after connection between the IF and the external IF is cut off, it is desirable to set the operation mode of the radiography controller 21 to the operation mode with relatively low power consumption described above. Thereby, ability of the medical vehicle 1A to charge the built-in power supply of the radiography device 2 is not less than power consumption of the radiography device 2.

It enables both synchronization of the medical vehicle 1A and the radiography device 2 and reliable charging of the built-in power supply of the radiography device 2.

6. Radiography Using Radiography System

Figure 6:
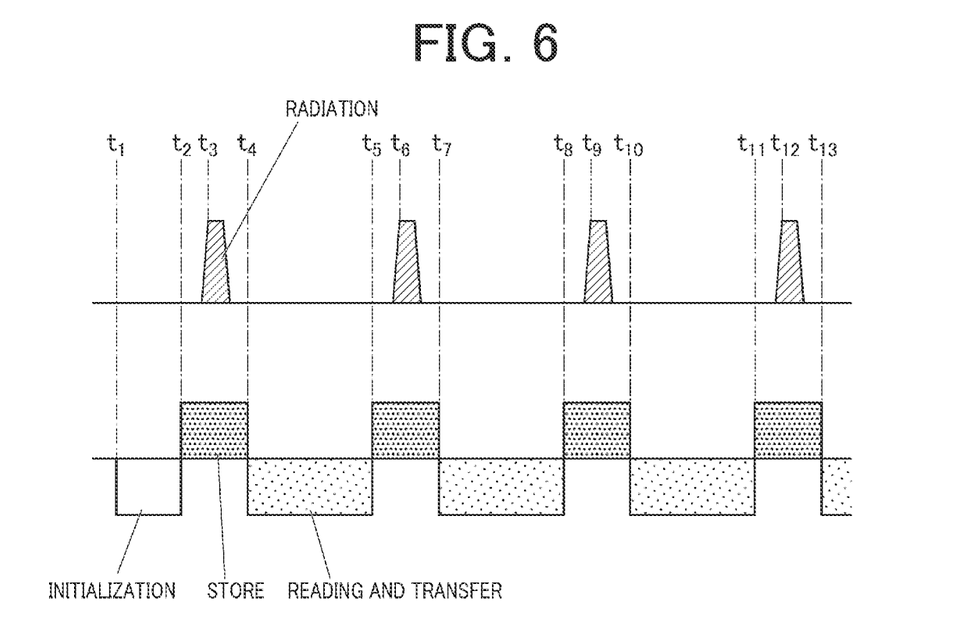
FIG. 6 is a timing chart showing operation of the radiography system of FIG. 1.

Next, a basic radiography operation performed by the radiography system 100 will be described. FIG. 6 is a timing chart showing operation of the radiography system 100.

6-1. Start of Operation

First, a user performs operation that triggers start of timekeeping by the radiation controller 11 of the radiation device 1 and the radiography controller 21 of the radiography device 2. For example, the user turns on devices of the radiography system 100. Then, the radiation controller 11 and the radiography controller 21 start timing respectively. If time points at which devices are turned on are different, a time point at which the radiography controller 21 of the radiation controller 11 starts timing differs from a time point at which the radiography controller 21 starts timing. Therefore, at this stage, a time point at which the radiation device 1 generates timekeeping information is different from a time point at which the radiography device 2 generates timekeeping information.

6-2. Connection of Radiation Device 1 and Radiography Device 2

When the radiation IF of the radiation device 1 is connected to the radiography IF of the radiography device 2 (it may be connected in advance), timekeeping information is transmitted from the parent device, which is one of the radiation device 1 and the radiography device 2, to the child device. The child device that receives the timekeeping information corrects operation of its own controller to match operation of the controller of the parent device. Thereby, they generate timekeeping information of the same value at the same time.

6-3. Disconnection of Radiation Device 1 and Radiography Device 2

The user then cuts connection between the external IF and the radiography IF (The user moves the radiography device 2 to a radiography position). Then, the child device comes into a state where it does not acquire timekeeping information. The parent device and the child device each keep time independently.

As described above, the radiation oscillator 11a and the radiography oscillator 21a of the embodiment generate clocks with high precision. Tolerance for difference between signals is widened. Accordingly, even after connection between the IF and the external IF is cut off, the controller of the child device repeats operation for generating a frame image or operation of generating radiation R while synchronizing with the radiography device without communicating with the outside.

6-4. Radiography Period

Then, the system 100 uses the controllers of the parent device and the child device of the radiation controller 11 and the radiography controller 21 to respectively control:

a time point when the radiation device 1 generates radiation R; and a time point when the radiography device 2 generates image data.

Specifically, as shown in FIG. 6, for example, when timekeeping information of the radiography controller 21 is a first predetermined value (t1) (when the first predetermined time (t1) elapses from start of timekeeping), the radiography device 2 enters an initialization state.

In the initialization state, the radiography controller 21 performs initialization. That is, the radiography controller 21 applies an ON voltage to each switch element of the radiation detector 22 to release a dark charge stored in each pixel to a signal line.

Depending on a configuration of the radiation detector elements of the radiography device 2, the radiography controller 21 performs initialization operation by releasing a stored charge when reading a charge.

Then, when timekeeping information generated by the radiography controller 21 reaches a second predetermined value (t2) that is larger than the first predetermined value (when the second predetermined time (t2) elapses from the start of timekeeping), the radiography device 2 enters an accumulation state.

In the accumulation state, the radiography controller 21 applies an off voltage to each scanning line to make the radiation detector 22 enter a state in which charges generated by the radiation detector elements can be accumulated in pixels. The radiography device 2 continues this accumulation state until timekeeping information generated by the radiography controller 21 reaches a fourth predetermined value (t4) that is larger than the second predetermined value (until the fourth predetermined time elapses from the start of timekeeping).

When timekeeping information generated by the radiation controller 11 reaches a third predetermined value (t3) that is larger than the second predetermined value and smaller than the fourth predetermined value (when the third predetermined time elapses from the start of timekeeping), the radiation device 1 irradiates, with radiation R, a subject and the radiography device 2 behind the subject. That is, the radiation device 1 applies radiation R during a period (t2 to t4) in which the radiography device 2 can accumulate charges.

During this time, the radiography device 2 is in the accumulation state. Accordingly, when the radiography device 2 receives radiation R, the radiography device 2 generates charges at radiation detector elements of the radiation detector 22 and accumulates it in pixels.

When timekeeping information generated by the radiography controller 21 reaches a fourth predetermined value (t4) that is larger than the third predetermined value (when the fourth predetermined time (t4) elapses from the start of timekeeping), the radiography device 2 enters a read/transfer state.

In the read/transfer state, the radiography controller 21 first applies an ON voltage to a switch element connected to each scanning line in the same flow as that of initialization. The radiography controller 21 releases a charge stored in each pixel to a signal line. Then, the radiography controller 21 makes the reader 23 read a signal value which is based on a charge flowing into the reader 23. The radiography controller 21 generates image data based on the read signal values.

In a case where the radiography mode is serial radiography, the radiography device 2 enters the accumulation state every time timekeeping information generated by the radiography oscillator 21a reaches a predetermined time (t5, t8, t11, . . . ). Then, the radiography device 2 enters the read/transfer state. The radiography device 2 repeats the series of operations by the number of frame images to be captured.

The radiation device 1 applies radiation R by the number of frame images to be captured every time timekeeping information generated by the radiation oscillator 11a reaches a predetermined time (t6, t9, t12, . . . ).

7. Radiography System, Etc.

Next, in addition to the above embodiments and modifications, various techniques that can be applied to the above system 100 (mobile radiography system 100A) will be described.

7-1. Still Radiography

The timing signals of the radiation device 1 and the radiography device 2 are for serial radiography. Accordingly, it is preferable that the system 100 (mobile radiography system 100A) can perform still radiography without a user being aware of synchronization of timing signals in a workflow.

Therefore, the controller of the child device may perform processing for synchronizing timing signals independently of processing for serial radiography. The controller adjusts radiation timing of radiation R in serial radiography to the timing signal.

In that case, the controller of the child device may use one of timing signals to perform still radiography. Alternatively, the controller may perform still radiography on a separate system.

Thus, still radiography can also be performed within a workflow. It improves usability.

7-2. Wired Communication

As a countermeasure for when radiography cannot be continued due to reasons such as inability to establish a wireless connection or lack of remaining power in the built-in power supply, radiography may be performed while the radiation device 1 and the radiography device 2 are connected by the communication cable 3. However, depending on an environment in which the system 100 (mobile radiography system 100A) is placed, when radiation R is applied for radiography during wired connection, the communication cable 3 picks up ambient electromagnetic noise. Noise can affect radiographic images.

Therefore, the system 100 (mobile radiography system 100A) may check a connection status of the communication cable 3 and a status of radio waves used for wireless communication. The system 100 may switch between radiography with a wired connection and radiography with a wireless connection depending on the status of radio waves. The system 100 may prioritize one of radiography with a wired connection and radiography with a wireless connection over the other, depending on a status of wireless connection.

Alternatively, the system 100 may prohibit wireless radiography during wired connection in view of effects of electromagnetic noise that may be picked up by the communication cable 3.

To prevent degradation of accuracy of synchronization, the system 100 may prioritize wired radiography regardless of the status of radio waves.

It prevents noise via the communication cable 3 from affecting radiographic images.

7-3. Marker

In a case where multiple external IFs (communication cable 3, cradle, etc.) are provided and may include external IFs for which timing signals cannot be synchronized, it is desirable to be able to determine at a glance to which external IF the radiography device 2 should be connected in order to synchronize timing signals in advance.

Therefore, a marker may be attached to the external IFs for which timing signals can be synchronized.

The external IF may notify a user that the timing signals can be synchronized by means other than the marker, such as sound, flashing or turning off of light, or change in color of emitted light.

A guide to means that can be synchronized may be displayed on, for example, a display (not shown) of the console 5.

Users can accurately distinguish the means that can be synchronized. It realizes a smooth workflow.

7-4. Permission to Switch Frame Rate

In a case where a frame rate of either or both of the radiation device 1 and the radiography device 2 is switched to a different frame rate in the middle of radiography, timing signals of the radiation device 1 and the radiography device 2 cannot keep synchronization.

Therefore, it is desirable to prohibit switching of frame rates while the IF of at least one of the radiation device 1 and the radiography device 2 is not connected to the external IF.

Instead of prohibiting the switching of frame rates, or while prohibiting the switching, it is desirable to inform a user of loss of synchronization.

7-5. Ranges of Radiography Conditions

In general, a radiation time of a control device for radiography can be discrete values of several milliseconds (e.g., 1 millisecond) to several seconds or tens of seconds (e.g., 10 seconds). Therefore, it is desirable that similar values can be selected in the system 100 (mobile radiography system 100A).

However, as already explained, in serial radiography, the radiation device 1 needs to apply radiation R during a period (t2 to t4) in which the radiography device 2 is in the accumulation state, in which the radiography device 2 can accumulate charges. For example, in a case where pulsed radiation R is applied 15 times per second so that 15 frames of images are generated per second, a period of radiation of pulsed radiation R (t3 to t6 in FIG. 6) and a period of generation of frames (t2 to t5 in FIG. 6) are about 66 milliseconds. A period of the accumulation state is even shorter than 66 milliseconds.

Therefore, if a radiation time up to several tens of seconds as described above is included in options, an afterimage of a previous frame will be reflected in a frame. An appropriate image cannot be obtained.

Therefore, the console 5 may switch ranges of a settable radiation time according to a set radiography mode.

Specifically, a radiation time range A (e.g., 1 millisecond to 10 seconds) used in still radiography and a radiation time range B (e.g., 3 milliseconds to 10 milliseconds) used in serial radiography are held in advance as a table. A relevant radiation time range is obtained from the table according to a set radiography mode. Suitability of a radiation time is determined by comparing a radiation time to be set with the obtained radiation time range. If the radiation time to be set is outside the radiation time range, the setting will not be permitted. If it is within the radiation time range, the setting will be permitted. Thus, permission for settings is controlled.

The console 5 may have a radiation time range that suits a frame rate of serial radiography.

A period of the accumulation state (t2 to t4) is shorter at higher frame rates than at lower frame rates. Therefore, a radiation time range that suits a frame rate is held in advance. A radiation time range that suits a set frame rate is obtained. Suitability is determined and permission for settings is controlled. Thus, appropriate images are generated for each frame rate.

The console 5 may have radiation time ranges that suit:
wired radiography in which radiography is performed while the radiation device 1 and the radiography device 2 are connected by the communication cable 3; and
wireless radiography where radiography is performed while they are not connected.

In wired radiography, a time point at which the radiation device 1 generates radiation R and a time point at which the radiography device 2 enters the accumulation state (t2 to t4) can be matched with a wire. Therefore, a difference between the time points is small. As a result, a radiation time range becomes wider. On the other hand, the difference between the time points tend to be larger in wireless radiography than in wired radiography. A radiation time range is narrower in wireless radiography than in wired radiography.

Therefore, the console 5 has radiation time ranges that suit wired radiography and wireless radiography. The console 5 acquires a radiation time range that suits a set radiography method (wired radiography or wireless radiography). The console 5 determines suitability and controls permission for settings. Thus, the console 5 generates appropriate images in each radiography method.

Control of permission for settings and determination of suitability according to radiography mode, frame rate, and wired and wireless radiography by the console 5 are explained above. The console 5 may provide a table in which two or more of them are combined to determine suitability and to control permission for settings.

A radiation time range is explained above. The console 5 may perform similar control for at least one of a tube voltage range, a tube current range, and a range of a product of tube current and time.

The tube 1b and the control device 1a are subjected to a longer load in serial radiography than in still radiography. It affects the life of the radiation device 1.

Therefore, the console 5 may determine suitability of a set tube voltage, a set tube current, and a set product of tube current and time to control permission for settings while making a tube voltage range, a tube current range, and a range of a product of tube current and time which can be used in serial radiography narrower than those that can be used in still radiography.

It reduces effect on the life of the radiation device 1.

The console 5 may have a table in which two or more of a tube voltage range, a tube current range, a range of a product of tube current and time, and a radiation time range are combined. Instead of having the ranges in the table, the console 5 may calculate the ranges using formulae.

A configuration of the console 5 having the above function is explained above. Alternatively, the control device 1*a* may have the above function. The console 5 and the control device 1*a* each may have the above function.

The console 5 and the control device 1*a* may share the above function. For example, in a case where a radiation time range for serial radiography is within a radiation time range for still radiography, the console 5 may have a function of determining suitability for serial radiography to control permission for settings, and the control device 1*a* may have a function of determining suitability for still radiography to control permission for settings.

7-6. Conversion of Product of Tube Current and Time to Tube Current and Radiation Time In general, a control device for radiography can select:
a kV/mA/sec mode in which a tube voltage, a tube current, and a radiation time are set respectively; and
a kV/mAs mode in which a tube voltage and a product of tube current and time (mAs) are set.

In the kV/mAs mode, the radiation control device divides a product of tube current and time (mAs) into a tube current (mA) and a radiation time (sec) in a predetermined method. The radiation control device controls a high voltage generator and a tube using a tube voltage, a tube current, and a radiation time.

In general, the maximum possible radiation time in radiography is several seconds or tens of seconds, which is very long. In order to divide a product of tube current and time (mAs) into a tube current (mA) and a radiation time (sec), if a tube current (mA) is determined such that mAs becomes a desired value after a maximum selectable radiation time is chosen, a radiation time of several seconds or tens of seconds is likely to be chosen. Longer radiation times are inappropriate because body movement of a patient during radiation is more likely to have effect. Therefore, such a division method in which a radiation time is prioritized (increased) over a tube current (mA) is generally not used. A division method in which a tube current (mA) is prioritized (increased) over a radiation time is used.

However, in serial radiography, in a case where the method in which a tube current (mA) is prioritized over a radiation time is used, the smallest radiation time among selectable radiation times tends to be selected. For example, in a case where a radiation time range is between 1 millisecond to 10 milliseconds, a value close to 1 millisecond tends to be selected. In general, it is known that a radiation waveform is not stable in cases where a radiation time is short. In radiography in which pulsed radiation R is applied multiple times, such as serial radiography, the instability of a radiation waveform causes difference between doses of pulsed radiation R. It causes a flicker of an image. Sometimes appropriate images cannot be obtained.

To avoid the problem, in the kV/mAs mode, in a case where a set radiography mode is still radiography, the control device 1*a* may select a division method in which a tube current (mA) is prioritized (increased) over a radiation time. In a case of serial radiography, the control device 1*a* may select a division method in which radiation time is prioritized (increased) over tube current (mA). The controller 1*a* divides a product of tube current and time (mAs) into a tube current (mA) and a radiation time (sec) using the selected method.

In that case, the maximum possible radiation time in serial radiography tends to be selected in serial radiography. As already explained, the maximum radiation time is much shorter (e.g. 10 milliseconds) in serial radiography than in still radiography. Body movement of a patient during radiation is unlikely to have effect. The problem that occurs when a division method in which a radiation time is prioritized (increased) over a tube current (mA) is selected for still radiography does not occur.

Thus, an appropriate tube current (mA) and an appropriate radiation time (sec) are automatically selected for each radiography mode. It improves ease of use for a radiographer and prevents unnecessary exposure to a subject in failed radiography.

A configuration in which the control device 1*a* has a division function is described above. Alternatively, the console 5 may have the division function.

The control device 1*a* or the console 5 may use the range table described in "7-5. RANGES OF RADIOGRAPHY CONDITIONS" as a radiation condition range and a tube current range used for division.

Advantageous Effect

Of the radiation device 1 and the radiography device 2 provided in the radiography system 100 (mobile radiography system 100A) of the embodiment described above, the child device includes:

the IF that can be connected to the external IF; and
the controller operated by the radiation device 1 based on timing signals from the external IF connected to the IF, while synchronizing with timing of repetition of operation by the parent device in serial radiography.

Even after connection between the IF and the external IF is cut off, the controller repeats operation for generating a frame image or operation of generating radiation R while synchronizing with the radiation device 1 without communicating with the outside.

Therefore, according to the radiography system 100 (mobile radiography system 100A), serial radiography is stably performed even while the radiation device 1 and the radiography device 2 are not connected to each other with the external IF such as the communication cable 3.

Although embodiments of the present invention have been described and illustrated in detail, the disclosed embodiments are made for purposes of illustration and example only and not limitation. The scope of the present invention should be interpreted by terms of the appended claims.

The entire disclosure of Japanese patent application No. 2020-214570, filed on Dec. 24, 2020, is incorporated herein by reference in its entirety.

What is claimed is:
1. A radiography system, comprising:
a radiation device that generates radiation in serial radiography;
a radiography device that generates a plurality of frame images in the serial radiography; and
a controller that controls synchronization between generation of the radiation by the radiation device and generation of the plurality of frame images by the radiography device, wherein the controller prohibits switching of a frame rate of the serial radiography in at least one of the radiation device and the radiography device after synchronization of the radiation device and the radiography device.

2. The radiography system according to claim 1, wherein the controller synchronizes the radiation device with the radiography device in a state that an interface unit of the radiation device and an interface unit of the radiography device are connected, and the controller prohibits the switching of the frame rates of the serial radiography when the radiation device and the radiography device are wirelessly connected after the synchronization of the radiation device and the radiography device.

3. The radiography system according to claim 2, wherein the controller prohibits the switching of the frame rate of the serial radiography when at least one of the interface unit of the radiation device and the interface unit of the radiography device are not connected by an external interface.

4. The radiography system according to claim 2, wherein the controller synchronizes the radiation device with the radiography device based on a timing signal generated by the radiation device or the radiography device.

5. The radiography system according to claim 1, wherein the controller performs a notification based on the prohibition of the switching of the frame rate of the serial radiography.

6. The radiography system according to claim 1, wherein the controller is provided in the radiation device.

7. The radiography system according to claim 6, wherein the radiation device is a medical vehicle.

8. A radiographic imaging methods, comprising:

synchronizing a radiation device that generates radiation with a radiography device that generates a plurality of frame images, in serial radiography; and prohibiting switching of a frame rate of the serial radiography in at least one of the radiation device and the radiography device after synchronization of the radiation device and the radiography device.

* * * * *